United States Patent [19]

Matsuzaki

[11] Patent Number: 5,239,364
[45] Date of Patent: Aug. 24, 1993

[54] LIGHT PHASE DIFFERENCE MEASURING METHOD USING AN INTERFEROMETER

[75] Inventor: Hiroshi Matsuzaki, Hachiouji, Japan

[73] Assignee: Olympus Optical Co., Ltd., Tokyo, Japan

[21] Appl. No.: 782,550

[22] Filed: Oct. 25, 1991

[30] Foreign Application Priority Data

Oct. 26, 1990 [JP] Japan .................. 2-289306

[51] Int. Cl.$^5$ .............................................. G01B 9/02
[52] U.S. Cl. ..................................... 356/360; 356/345
[58] Field of Search ............... 356/345, 355, 357, 358, 356/359, 360, 361

[56] References Cited

U.S. PATENT DOCUMENTS

4,169,980 10/1979 Zanoni ................. 356/345
4,630,926 12/1986 Tanaka et al. ......... 356/357

FOREIGN PATENT DOCUMENTS

0244204 3/1987 Fed. Rep. of Germany ...... 356/361
52-110684 9/1977 Japan .
0118205 5/1987 Japan ................. 356/359

OTHER PUBLICATIONS

Subfringe Interferometry Fundamentals (Optics 13 (1984 55) pp. 55-65.

Primary Examiner—Samuel A. Turner
Attorney, Agent, or Firm—Cushman, Darby & Cushman

[57] ABSTRACT

A light phase difference measuring method including: a step of splitting a coherent light beam into two light beams; a step of allowing one of the two light beams to be transmitted or reflected through or on a sample to be measured; a step of producing interference fringes having a high spatial frequency by inclining the other light beam relative to the optical path for incidence thereof so as to overlap these two light beams with each other; a step for detecting locations of points having locally maximum lightness and points having locally minimum lightness on the interference fringes; and a step for measuring locations of the points having locally maximum lightness and the points having locally minimum lightness or a spatial frequency for determining a phase difference between the two light beams. This measuring method makes it possible to always input correct data into a processing circuit.

3 Claims, 4 Drawing Sheets

LIGHT PHASE DIFFERENCE MEASURING METHOD USING AN INTERFEROMETER

BACKGROUND OF THE INVENTION a) Field of the Invention:

The present invention relates to a light phase difference measuring method using an interferometer.

b) Description of the Prior Art:

Available as the conventional phase difference measuring methods using interferometers are the fringe scanning method, heterodyne method, Fourier transform method, etc. (Optics 13 (1984) 55) which are used for measuring surface roughness, aspherical surfaces, refractive index distributions in unhomogenous media and so on. For measurements with higher accuracy, these conventional measuring methods require measurements of intermediate intensities between locally maximum lightness and locally minimum lightness in intensity distributions on produced interference fringes. When light receiving elements used for measurement have insufficient linearities, when interference fringes are affected by noise or when contrast is low on interference fringes in measurements of the intermediate intensities, however, the conventional methods do not permit accurate measurement of intensity distributions and may provide inaccurate values of phases.

SUMMARY OF THE INVENTION

In view of the problem described above, it is a primary object of the present invention to provide a light phase difference measuring method using an interferometer which is adapted to permit an accurate determination of phase differences without measuring intermediate intensities on interference fringes constituting the cause for errors.

In order to attain the object described above, the light phase difference measuring method according to the present invention is adapted to permit a determination of a phase difference by: splitting a coherent light beam into two light beams; allowing one of the two light beams to be transmitted or to be reflected through or by a sample to be measured; using the other light beam as a reference beam; producing interference fringes having a high spatial frequency as a carrier by inclining the reference beam relative to the optic axis of an optical path for incidence thereof; detecting locations of points having locally maximum lightness and locations of points having locally minimum lightness in an intensity distribution on the interference fringes; and measuring the locations or the spatial frequency thereof.

Since the light phase difference measuring method according to the present invention is adapted to read only the locally maximum lightness and the locally minimum lightness in the intensity distribution on the interference fringes, the measuring method makes it possible to input accurate data into a processing circuit even when contrast is low on the interference fringes, when the interference fringes are affected by noise or when the light receiving element used has low linearity.

This and other objects as well as the features and advantages of the present invention will become apparent from the following detailed description of the preferred embodiments when taken in conjunction with the accompanying drawings.

DESCRIPTION OF THE PREFERRED EMBODIMENTS

Figure 1:
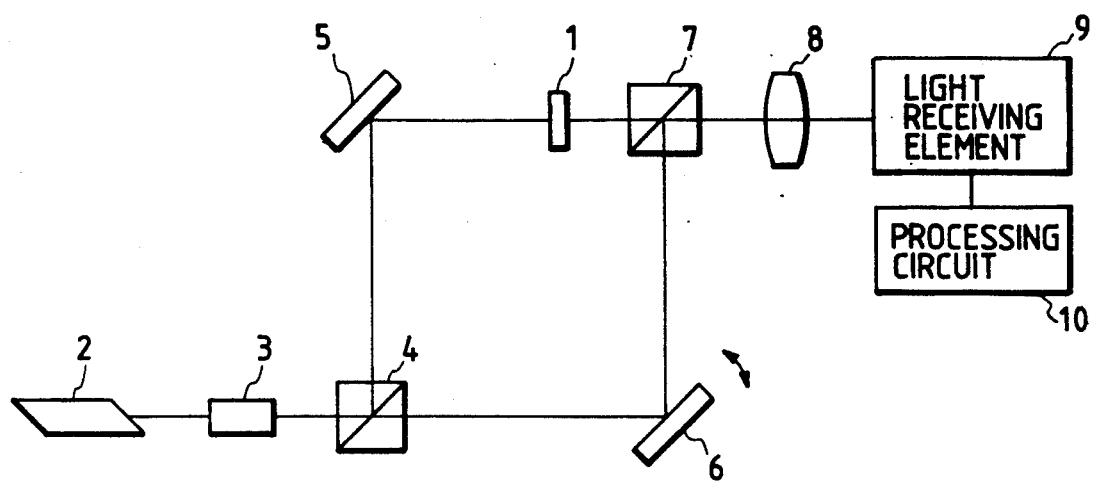
FIG. 1 is a block diagram illustrating an optical system arranged in an interferometer which is to be used for carrying out Embodiment 1 of the light phase difference measuring method according to the present invention.

Prior to description of the embodiments of the light phase difference measuring method according to the present invention, the principle of this method will be explained below:

When a spatial frequency of interference fringes, which are produced as a carrier in the direction perpendicular to the x axis, is represented by $f_o$, an intensity distribution $g(x)$ on a straight line which is traced across the interference fringes so as to be parallel with the x axis is expressed as follows:

$$g(x) = a(x) + b(x) \cos[2\pi f_o \cdot x + \Phi(x)] \quad (1).$$

This intensity distribution represents points which are produced at narrow intervals as the carrier of the spatial frequency $f_o$ and have phases spatially modulated depending on a phase $\Phi(x)$ of a sample. In the intensity distribution which is expressed as described above, a condition for a point to have locally maximum or minimum lightness is:

$$\cos[2\pi f_o \cdot x + \Phi(x)] = 1 \text{ (for a point to have locally maximum lightness)}$$

or $$\cos[2\pi f_o \cdot x + \Phi(x)] = -1 \text{ (for a point to have locally minimum lightness)} \quad (2).$$

Let us assume that m represents an integer, an adequate interference fringe is selected as a standard, and a location of a point having a locally maximum lightness on the m-th fringe is represented by $x_1(m)$ or a location of a point having locally minimum lightness on the m-th fringe is designated by $x_0(m)$. Then, formula (2) can be transformed as follows:

$2\pi f_0 \cdot x_1(m) + \Phi(x_1(m)) = 2\pi m$ (for a point to have locally maximum lightness)

or $2\pi f_0 \cdot x_0(m) + \Phi(x_0(m)) = 2\pi(m + \frac{1}{2})$ (for a point to have locally minimum lightness)     (3).

When the spatial frequency $f_0$ of the carrier is determined in advance, it is therefore possible to calculate a value of a phase at the point according to the following formula (4) by measuring the location $x_1$ (m) of the point having locally maximum lightness or the location $x_0$(m) of the point having locally minimum lightness in the intensity distribution on the interference fringes:

$$\Phi(x_1(m)) = 2\pi(m - f_0 \cdot x) \quad (4)$$

or $$\Phi(x_0(m)) = 2\pi(m + 1/2 - f_0 \cdot x)$$

By selecting a spatial frequency which is sufficiently high, the phase difference measurement can have enhanced resolution and provide measuring results with higher accuracy.

Further, by differentiating both sides of formula (4) by x yields:

$$d\Phi/dx = 2\pi[(dm/dx) - f_0] \quad (5).$$

Since (dm/dx) used in the formula (5) expresses the spatial frequency at the points of interest, (d$\Phi$/dx) can be determined by measuring the spatial frequency at this point and it is possible to determine the phase difference $\Phi$ by integrating (d$\Phi$/dx).

In this case, however, the spatial frequency is actually measured as an average value within a certain definite range and variation of the phase must be small as compared with $f_0$.

The terms a(x) and b(x) representing noise and nonuniformity of intensity in g(x) in formula (1) disappear in formulae (4) and (5). Therefore, the light phase difference measuring method according to the present invention makes it possible to measure a phase difference accurately even on interference fringes affected by noise or intensity non ununiformity as expressed by the formula (1).

Now, the light phase difference measuring method according to the present invention will be described in detail below with reference to the preferred embodiments illustrated in the accompanying drawings.

FIG. 1 shows a block diagram of an optical system arranged in a two-beam interferometer which is to be used for Embodiment 1 of the present invention. In this drawing, the reference numeral 1 represents a sample to be measured. For measuring a phase difference in a transmission light beam (for example, for measuring refractive index distribution), the interferometer must be of Mach-Zehnder type shown in FIG. 1. The reference numeral 2 designates a light source emitting a coherent light beam, which is to be expanded in the diameter thereof by a beam expander 3 and then split into two beams by a beam splitter 4. One of the beams is reflected by a planar reflecting mirror 5 and travels along another optical path so as to be transmitted through the sample 1. The other light beam is used as a reference beam, which is reflected by a planar reflecting mirror 6 rotatable for turning the optical path and overlapped by a beam splitter 7 with the light beam having been transmitted through the sample 1 for producing interference fringes. The interference fringes thus produced are imaged by an imaging optical system 8 onto a light receiving element 9. The reference numeral 10 represents a processing circuit for calculating a phase difference on the basis of data provided from the light receiving element 9.

Now, functions of the two-beam interferometer used for carrying out Embodiment 1 of the present invention will be described below:

By inclining the planar reflecting mirror 6 at an angle of $\theta$ in FIG. 1, a phase difference is produced between the two light beams so as to produce interference fringes as a carrier having a high spatial frequency. The spatial frequency of the carrier can be calculated from the inclination angle $\theta$ of the planar reflecting mirror 6 or determined by measuring intervals of interference fringes which are actually produced with the sample 1 removed from the optical system.

Figure 2:
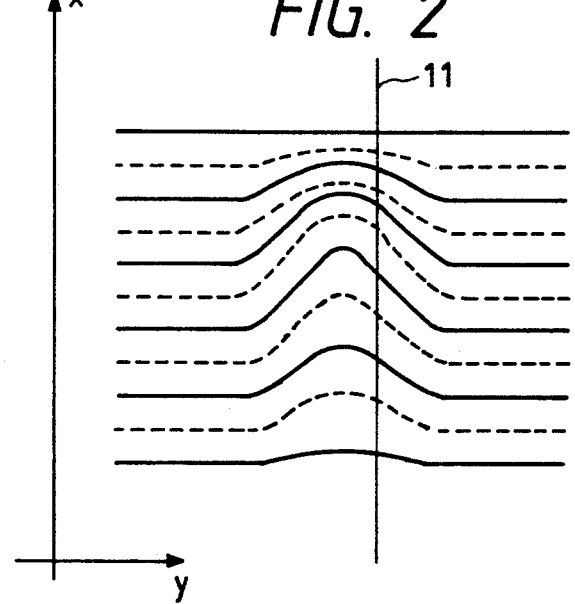
FIG. 2 is a diagram illustrating interference fringes produced by the optical system shown in FIG. 1.
Figure 3:
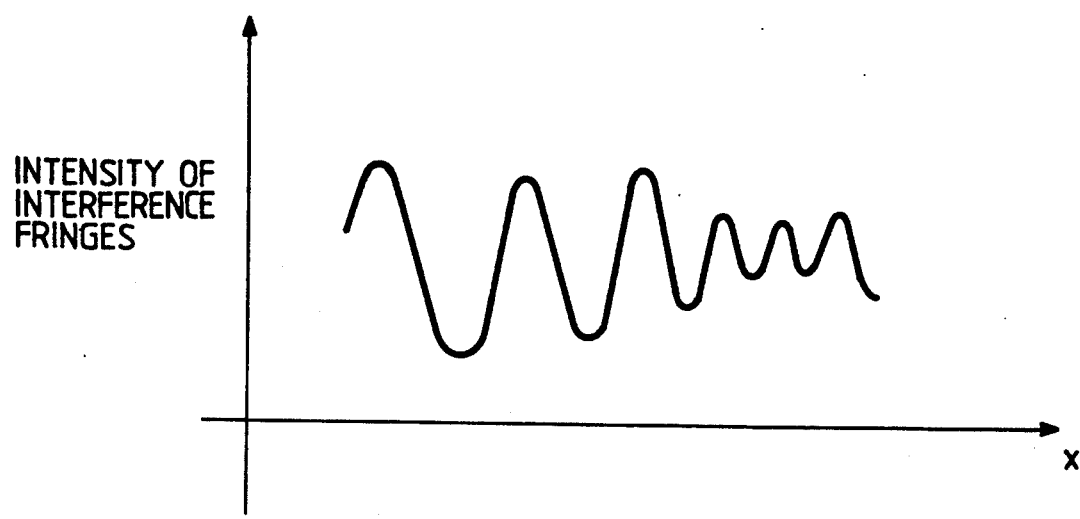
FIG. 3 is a graph illustrating an intensity distribution on a straight line which is set across the interference fringes as shown in FIG. 2.
Figure 4:
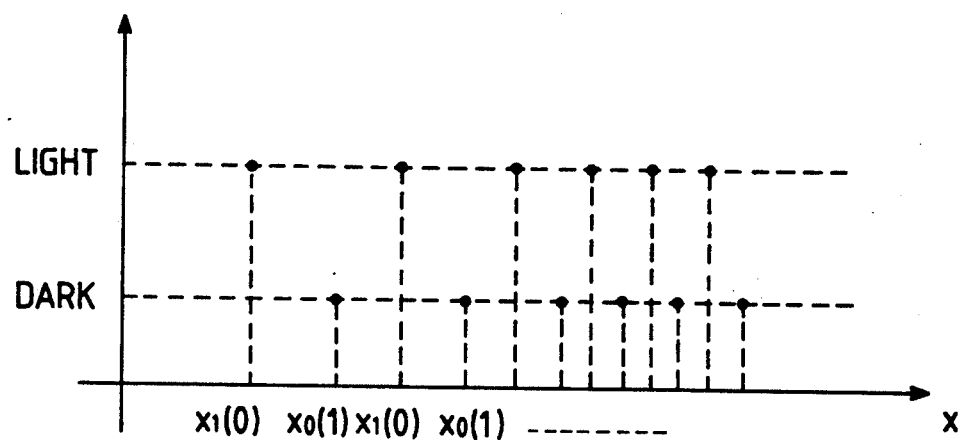
FIG. 4 is a graph illustrating locations of points having locally maximum lightness and locations of points having locally minimum lightness in the intensity distribution on the interference fringes.

The interference fringes produced by the optical system are shown schematically in FIG. 2, wherein solid lines represent fringes having locally maximum lightness and the dashed lines represent fringes having locally minimum lightness in intensity distribution. FIG. 3 shows a graph illustrating an intensity distribution on a measuring line 11 which is traced across the interference fringes so as to be parallel with the x axis set in the direction perpendicular to the interference fringes. In the intensity distribution on actual interference fringes, averages of intensity and contrast are varied from fringes to fringes, as shown in FIG. 3, due to the non ununiformity of light quantity, etc. which are represented by a(x) and b(x) in formula (1). FIG. 4 shows the locations of points, on the line 11, having locally maximum lightness and points having locally minimum lightness which are determined from the intensity variation curve illustrated in FIG. 3.

Let us assume that the location of a standard point is represented by $x_1$ (0), and the locations of the points having locally minimum lightness and locally maximum lightness are designated sequentially by $x_0$ (0), $x_1$ (1), $x_0$ (1), ... $x_1$ (m), $x_0$ (m) respectively. From the locations $x_1$ (m) and $x_0$(m) thus determined, it is possible to calculate the phase difference $\Phi$(x) by using formula (4).

Alternately, when a range of $x_1$ (m)$\pm\Delta x$ wherein the phase of the light beam having passed through the sample 1 varies linearly is selected and a number n($x_1$ (m)) of points having locally maximum lightness or locally minimum lightness in intensity distribution within the range of $x_1$ (m)$-\Delta x \leq x \leq x_1$ (m)$+\Delta x$ is measured, n($x_1$ (m))/2$\Delta x$ is obtained as the spatial frequency at $x_1$ (m). It is therefore possible to determine d $\Phi(x_1$ (m))/dx through calculation by formula (5). The phase difference $\Phi$ (x) can be determined by numerically integrating the values of a series of d$\Phi(x_1$ (m))/dx obtained as described above.

Figure 5:
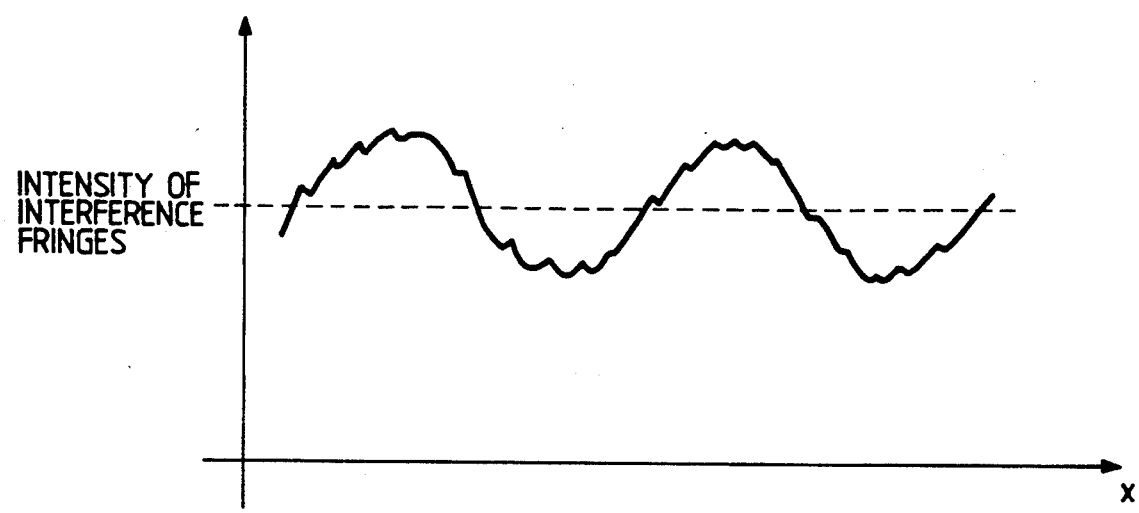
FIG. 5 is a graph illustrating an intensity distribution on interference fringes affected by remarkable noise.
Figure 6:
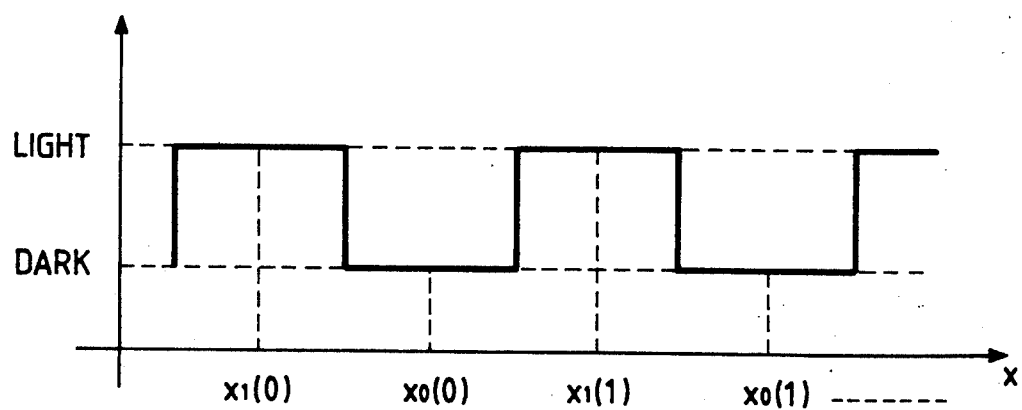
FIG. 6 is a graph illustrating points having locally maximum lightness and points having locally minimum lightness which are obtained by processing the graph shown in FIG. 5 with a certain threshold value as a boundary.

So long as noise is low enough to permit easy determination of the locations of the points having locally maximum lightness and the points having locally minimum lightness, it is general to use the method which detects the points having locally maximum lightness and the points having locally minimum lightness in intensity variation by scanning the intensity variation on the interference fringes. When noise is high enough to produce a plurality of points having locally maximum lightness or locally minimum lightness at a single location, however, it is not easy to detect these points accurately. In such a case, it is conceivable to adopt the method described below: that is to say, a threshold value is selected as a boundary as indicated by the dashed line in FIG. 5 for classifying these points into light points and dark points so that $x_1(0)$, $x_1(1)$, . . . are detected as the points having locally maximum lightness and $x_0(0)$, $x_0(1)$, . . . are detected as points having locally minimum lightness.

Further, though noise may cause errors in classifying the points located in the vicinity of the threshold value, such errors can be reduced by preliminarily filtering the data provided from the light receiving element 9 so as to eliminate noise containing high-frequency components from the interference fringes.

Figure 7:
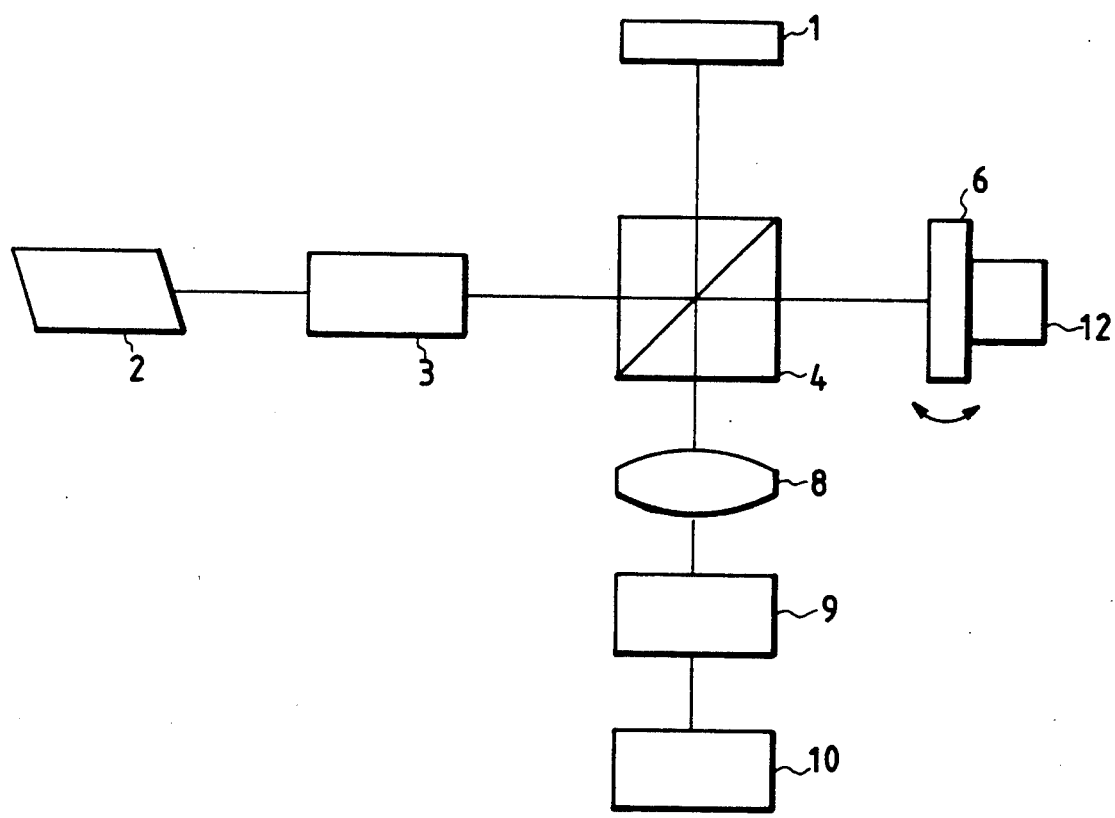
FIG. 7 is a block diagram illustrating an optical system arranged in an interferometer which is to be used for carrying out Embodiment 2 of the light phase difference measuring method according to the present invention.

Embodiment 1 which is adapted to measure a phase difference in the light beam having been transmitted through the sample 1 uses the Mach-Zehnder interferometer. When a phase difference in a reflection light is to be determined, for example, the interferometer need not be of the Mach-Zehnder type, but may be of another type, for example, Michelson type interferometer shown in FIG. 7 which permits measuring a phase difference according to a principle similar to that of the Mach-Zehnder interferometer. The optical system arranged in the interferometer to be used for Embodiment 2 of the present invention has a configuration which is substantially the same as that illustrated in FIG. 1, and is adapted to allow to change the optical path difference between the sample beam and the reference beam by arranging a piezoelectric element on the planar reflecting mirror 6. Accordingly, Embodiment 2 is adapted to permit performing not only the measurements with higher accuracy but also the scanning interference fringes.

What is claimed is:

1. A light phase difference measuring method utilizing an interferometer in which a two-beam interferometer is used for measuring a phase state from interference fringes produced by recombining coherent light divided into two light waves, comprising the steps of:

placing a sample to be measured in an optical path for one of said two light waves and producing a plurality of interference fringes for carriers by inclining an optical path of the other of said two light waves;

detecting locations of points having locally maximum lightness and other points having locally minimum lightness in intensity distribution of said interference fringes before said sample is placed in the optical path;

detecting the locations of points having locally maximum lightness and other points having locally minimum lightness in intensity distribution of said interference fringes after said sample is placed in the optical path; and determining a phase difference between said two light waves by measuring the amount of shift of the locations of points before and after said sample is placed in the optical path.

2. A light phase difference measuring method utilizing an interferometer in which a two-beam interferometer is used for measuring a phase state from interference fringes produced by recombining coherent light divided into two light waves, comprising the steps of:

placing a sample to be measured in an optical path for one of said two light waves and producing a plurality of interference fringes for carriers by inclining the other of said two light waves;

calculating a spatial frequency of a carrier from spacing of said interference fringes produced before said sample is introduced in the optical path;

detecting locations of points having locally maximum lightness and other points having locally minimum lightness in intensity distribution of said interference fringes before said sample is placed in the optical path;

detecting locations of points having locally maximum lightness and other points having locally minimum lightness in intensity distribution of said interference fringes after said sample is introduced in the optical path;

calculating gradients between values of phases from the amount of shift of the location of points before and after said sample is placed in he optical path; and integrating the gradients between said values of phases by using the spatial frequency of said carrier for determining a phase difference between said two light waves.

3. A light phase difference measuring method using an interferometer in which a two-beam interferometer is used for measuring a phase state from interference fringes produced by splitting coherent light into two light waves and allowing one light wave to be transmitted and reflected by a sample to be measured and the other light wave is reflected, as a reference light wave, from at least one planar reflecting mirror, said one light wave being recombined with said other light wave, said method comprising the steps of:

producing a number of interference fringes for carriers by inclining said planar reflector mirror so as to deflect said reference light wave prior to said sample being introduced in an optical path;

detecting locations of points having locally maximum lightness and other points having locally minimum lightness in intensity distribution of said interference fringes prior to said sample being introduced in the optical path;

detecting locations of points having locally maximum lightness and other points having locally minimum lightness in intensity distribution of said interference fringes after said sample is placed in the optical path;

calculating gradients between values of phases from the amount of shift of the location of points before and after said sample is introduced in the optical path; and integrating the gradients between said values and phases by using a spatial frequency of a carrier calculated from inclination of said planar reflecting mirror for determining a phase difference between said two light waves.

* * * * *